United States Patent
Du et al.

(10) Patent No.: US 8,311,297 B2
(45) Date of Patent: Nov. 13, 2012

(54) METHOD AND APPARATUS FOR IMPLEMENTING DOPPLER SCAN CONVERSION

(75) Inventors: Yajun Du, Shenzhen (CN); Jianyong Wang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 980 days.

(21) Appl. No.: 12/243,666

(22) Filed: Oct. 1, 2008

(65) Prior Publication Data

US 2009/0156938 A1    Jun. 18, 2009

(51) Int. Cl.
*G06K 9/00* (2006.01)

(52) U.S. Cl. ....................................... 382/128

(58) Field of Classification Search ............... 382/100, 382/128, 129, 130, 131; 600/407, 437, 440, 600/441, 453, 455, 457; 367/87, 90, 94; 342/84, 98, 99, 171

See application file for complete search history.

(56) References Cited

U.S. PATENT DOCUMENTS

| | | | | |
|---|---|---|---|---|
| 5,127,409 A | * | 7/1992 | Daigle | 600/443 |
| 5,379,771 A | * | 1/1995 | Kawasaki et al. | 600/456 |
| 5,872,769 A | | 2/1999 | Caldara et al. | |
| 6,086,539 A | * | 7/2000 | Guracar et al. | 600/453 |
| 6,508,763 B1 | | 1/2003 | Urbano et al. | |
| 6,733,454 B1 | | 5/2004 | Bakircioglu et al. | |
| 2004/0193047 A1 | * | 9/2004 | Pelissier et al. | 600/437 |
| 2005/0222506 A1 | * | 10/2005 | Takimoto et al. | 600/455 |
| 2007/0282203 A1 | * | 12/2007 | Baba et al. | 600/453 |
| 2009/0149759 A1 | * | 6/2009 | Baba et al. | 600/454 |
| 2010/0286522 A1 | * | 11/2010 | Beach et al. | 600/441 |

FOREIGN PATENT DOCUMENTS

| | | |
|---|---|---|
| CN | 101002972 A | 7/2007 |
| WO | 0045881 | 8/2000 |
| WO | 2004019766 A3 | 3/2004 |

* cited by examiner

*Primary Examiner* — Anand Bhatnagar

(74) *Attorney, Agent, or Firm* — Kory D. Christensen; Stoel Rives LLP

(57) ABSTRACT

A method for Doppler scan conversion includes storing coded envelope values together with spectrum data in a memory out of a logic device with a large capacity, which increases the number of envelopes stored, reduces the use of the restricted embedded memory resources, and can also achieve the envelope switching more flexibly. If the number of envelopes is not greater than the difference between the bit width of the memory and that of the spectrum data, the increase in the number of envelopes will not increase significantly the logic resources or affect the efficiency of the system.

16 Claims, 5 Drawing Sheets

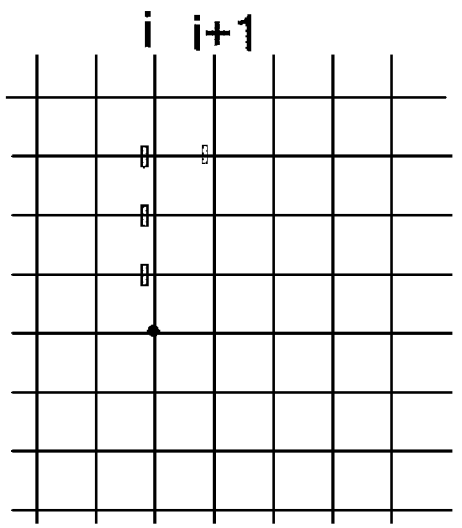
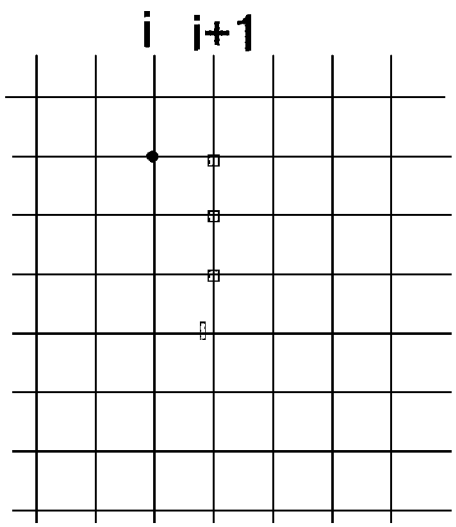
FIG. 5(a)  FIG. 5(b)
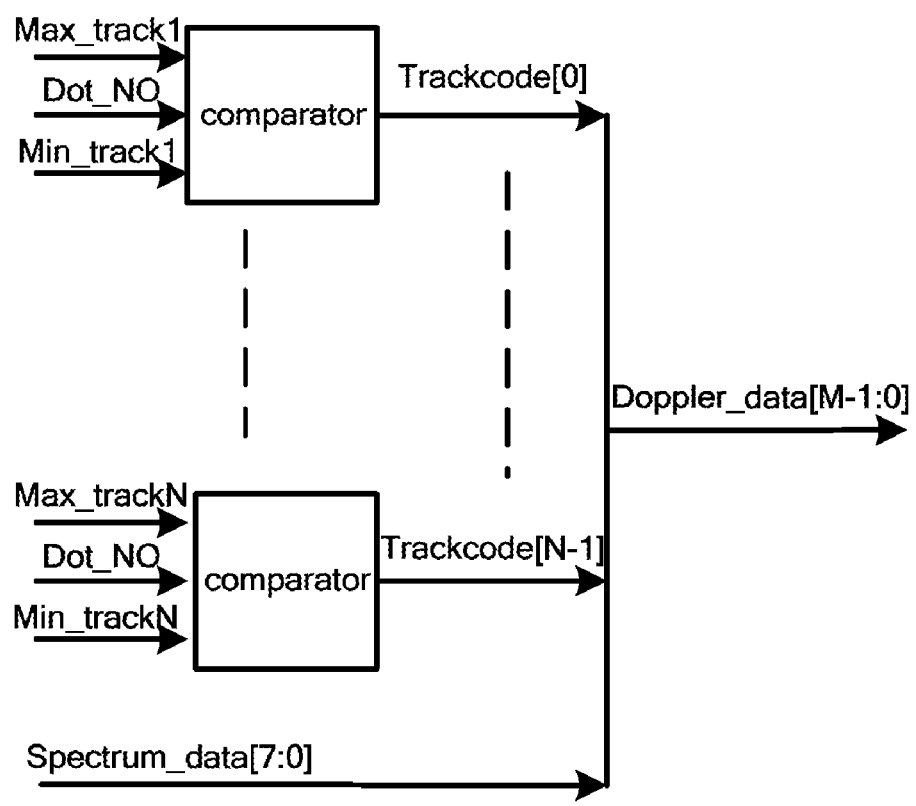
FIG.6

METHOD AND APPARATUS FOR IMPLEMENTING DOPPLER SCAN CONVERSION

CROSS-REFERENCE TO RELATED APPLICATIONS

This application claims priority to Chinese Patent Application No. 200710300801.x, filed on Dec. 18, 2007, for "Method and Apparatus for Implementing Doppler Scan Conversion," the disclosure of which is fully incorporated herein by reference.

TECHNICAL FIELD

This disclosure relates to scan conversion in an ultrasonic imaging system and, in particular, to a method and apparatus for implementing Doppler scan conversion.

BRIEF SUMMARY

A flexible and efficient implementation for Doppler scan conversion is disclosed.

BRIEF DESCRIPTION OF THE DRAWINGS

FIG. 5 is a schematic diagram of an implementation of envelope alignment;
FIG. 6 is a block diagram of an implementation of envelope encoding and spectrum data combination according to one embodiment of the present disclosure.

DETAILED DESCRIPTION

Doctors can determine whether abnormalities exist in the blood stream of a subject through ultrasonic Doppler inspection. Since there is a section of flow velocity of the blood in a radial direction in the vessels, various frequency components are contained in an echo signal. A spectrogram is generally employed for displaying the frequency components in an ultrasonic diagnosis instrument. In a spectrogram, the vertical axis represents a Doppler frequency corresponding to the velocity of the blood flow; the horizontal axis represents time. The grey level of pixels in the spectrogram represents the size of each of the frequency components corresponding to the time.

Figure 1:
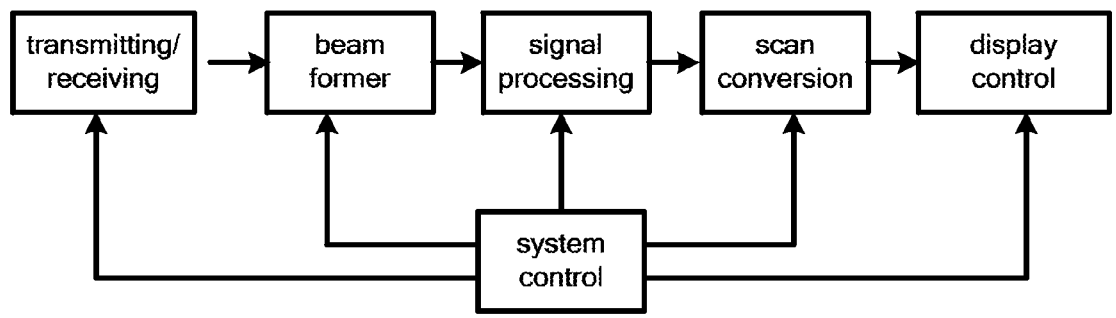
FIG. 1 is a block diagram of an ultrasonic system.
Figure 2:
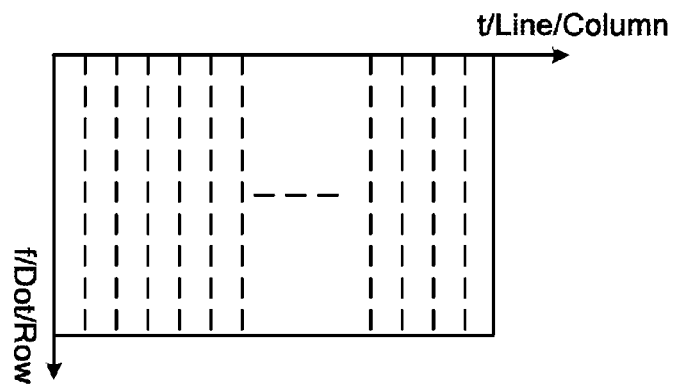
FIG. 2 is a data structure in a scan conversion memory.

In the ultrasonic system shown in FIG. 1, before an ultrasonic image is displayed, an echo signal generated through vertical scanning at the front end is received and then goes through a beam former and signal processing to obtain line data for an image. The line data is temporarily stored in a scan conversion memory in data structure as shown in FIG. 2, and then is read out in rows in a horizontally scanned VGA time sequence and sent to a display circuit after going through other relevant processes. Such a processing is referred to as the "scan conversion" of an ultrasonic image.

The ultrasonic image is operated in columns when being written into the scan conversion memory, i.e. each of the columns in the scan conversion memory stores a line of the image data, the column address corresponding to the horizontal coordinate (time: t) of the image displayed on the screen. The image data is operated in rows when being read out from the scan conversion memory, i.e. a row consisting of all the image dots in different lines at the same frequency is read out each time in the VGA time sequence, the row address corresponding to the vertical coordinate (frequency: f) of the image displayed on the screen.

Apart from having the same functions as those in other scan conversions of an ultrasonic image, the Doppler scan conversion further includes envelope superposition. Envelope superposition means that some useful envelope information (such as maximum frequency, etc.) extracted from the spectrogram is superposed on the spectrogram, such that doctors are able to observe the spectrogram more directly and clearly. Such envelope information is obtained through the signal processing in the front end of the ultrasonic system and sent to the display circuit after being superposed on the spectrogram in the scan conversion.

Figure 3:
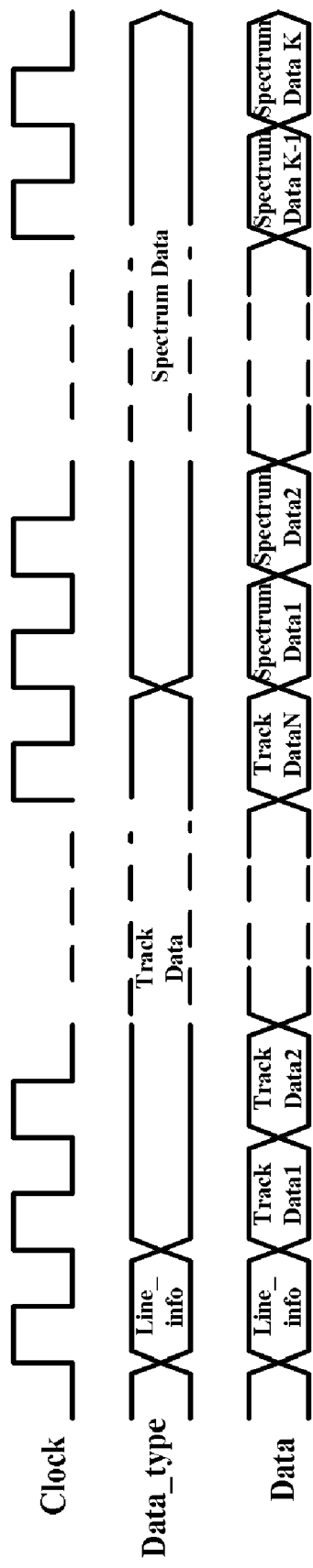
FIG. 3 is a timing diagram of a transmission time sequence of Doppler data.

The spectrum data and envelope value obtained through signal processing are transmitted to the scan conversion process in the time sequence as shown in FIG. 3. In one embodiment, the envelope value represents the location of the envelope in the vertical axis (frequency direction) of the spectrogram of the current line, and the spectrum data represents the size of the component of the frequency of the current line, the value of the spectrum data being the grey level of the dot corresponding to said spectrum data finally displayed. In one embodiment, the value corresponding to the currently displayed row number is compared with the envelope value. If the value corresponding to the currently displayed row number equals the envelope value, the current dot on the Doppler image shall be deemed to coincide with the envelope and thereby the value on this dot shall be displayed as the grey level of the corresponding envelope.

In general, there are three ways of implementing Doppler scan conversion. The first way is to perform the envelope superposition before the Doppler spectrum data is written into the scan conversion memory, write the envelope-superposed image data into the scan conversion memory, read out the image data in rows in the horizontally scanned VGA time sequence, and then send it to the display circuit. In this implementation, after the envelope superposition is performed, the value of the envelope having the highest priority level shall overlay the spectrum data at the location where the envelope having the highest priority level lies, thereby losing the spectrum data and the values of other envelopes at this location. It is thus impossible to implement the real-time and flexible envelope switching. Only after a period of time lapses after the envelope switching and until the new Doppler data have overlaid the current image data stored in the scan conversion memory can the image after switching be displayed.

The second way is to store the Doppler spectrum data together with the envelope data in the scan conversion memory, and then read out a row of spectrum data in the VGA time sequence and simultaneously read out all the envelope dots on the scanning line where each of the spectrum data dots lies to perform the envelope superposition, and thereafter send the envelope-superposed image data to the display circuit. In this implementation, since each of the pixel dots sent to the display circuit needs to determine whether there is an envelope dot needing superposition and the envelopes may not be restricted to one type, the scan conversion memory is required to have a huge bandwidth, and there cannot be too many types of envelopes.

The third way is to store the envelope data in FPGA (Field Programmable Gate Array) embedded RAMs, each type of envelope being stored in a different RAM, read out the spectrum data in rows in the VGA time sequence and simultaneously read out from all the RAMs all the envelope dots corresponding to each spectrum data dot to perform the envelope superposition to obtain the envelope-superposed image data, and send it to the display circuit. In this implementation, using the FPGA embedded memory to store envelope waveforms, due to the restricted resources in the FPGA-embedded memory, it is often impossible to reserve more envelopes and thus, the number of envelopes that can be displayed is significantly limited.

What is needed is a method for implementing Doppler scan conversion that minimizes or eliminates the aforementioned problems. According to one aspect of the present disclosure, the coded envelope values together with spectrum data are stored in a memory out of a logic device with a large capacity. The use of such a memory with a large capacity instead of the embedded memory with restricted resources increases the number of envelopes stored, reduces the use of the restricted embedded memory resources, and can achieve more flexibly the envelope switching. If number of envelopes is not greater than the difference between the bit width of the memory and that of the spectrum data, the increase in the number of envelopes shall not increase significantly the logic resources or affect the efficiency of the system.

According to an aspect of the present disclosure, there is provided a method for Doppler scan conversion. In one embodiment, the method includes caching image data of a current Doppler line, which includes spectrum data and values of N types of envelopes, in an embedded memory of a logic device. The method may also include comparing a value of each type of the envelopes of the current Doppler line with that of the same type of envelope of a neighboring Doppler line for envelope alignment to obtain starting point value Min_track(j) and end point value Max_track(j) of line section of each type of the envelopes of the current Doppler line, wherein j is the serial number of the envelope, and j=0, 1, 2, . . . , N−1, and registering the starting point value Min_track (j) and the end point value Max_track(j) of the line section of each type of the envelopes of the current Doppler line in an internal register of the logic device.

The method may further include reading out the spectrum data of the current Doppler line as well as the starting point value Min_track(j) and the end point value Max_track(j) of the line section of each type of the envelopes of the current Doppler line from the embedded memory of the logic device. With respect to each of the spectrum data dots on the current Doppler line, within the transmission clock cycle corresponding to each of the spectrum data dots and dot by dot, the method may include the following steps:

(1) calculating the serial number Dot_NO=i+1 of a current spectrum data dot on the current Doppler line, wherein i=0, 1, 2, . . . , K−1, and K is the number of the spectrum data dots on the current Doppler line;

(2) comparing the Dot_NO value corresponding to the current spectrum data dot on the current Doppler line with the starting point value Min_track(j) and the end point value Max_track(j) of the line section of each type of the envelopes of the current Doppler line; if the Dot_NO value corresponding to the current spectrum data dot on the current Doppler line is between the starting point value Min_track(j) and the end point value Max_track(j) of line section of a certain type of envelope of the current Doppler line, an envelope code Track_code[j] corresponding to that type of envelope is 1; otherwise the envelope code Track_code[j] corresponding to that type of envelope is 0; whereby a N-bit envelope code Track_code[N−1:0] is obtained; and (3) combining the N-bit envelope code Track_code[N−1:0] with the spectrum data value corresponding to the current spectrum data dot on the current Doppler line to obtain combined Doppler data, and storing the combined Doppler data in a scan conversion memory, wherein the number N of the types of the envelopes is smaller than difference between bit width of the scan conversion memory and that of the spectrum data.

In one embodiment, the number N of the types of the envelopes is smaller than the bit width of the scan conversion memory minus eight.

In one embodiment, the embedded memory may be an FPGA embedded memory, a CPLD embedded memory, or an ASIC embedded memory.

The method may further include the steps of reading out the combined Doppler data from the scan conversion memory; performing a logic operation on the N-bit envelope code Track_code[N−1:0] in the combined Doppler data and a N-bit selective value for envelope switching Track_switch[N−1:0] set by the system to obtain a N-bit envelope code selected by envelope switching Switch_out[N−1:0]; sending the N-bit envelope code selected by envelope switching Switch_out [N−1:0] to a N-bit priority encoder to obtain a L-bit priority-encoded envelope value Encode[L−1:0], wherein L=log 2N+1; sending the L-bit priority-encoded envelope value Encode[L−1:0] to a 1-of-N+1 selector to output the envelope value which is finally chosen to display among N types of the envelopes or the spectrum data value to a display module for displaying.

In one embodiment, the logic operation is a "bit and &" operation.

According to another aspect of the present disclosure, there is provided an apparatus for Doppler scan conversion, including a line-caching module for caching image data of a current Doppler line, which includes spectrum data and values of N types of envelopes, in an embedded memory of a logic device. The apparatus may further include an envelope alignment module for comparing value of each type of the envelopes of the current Doppler line with that of the same type of envelop of a neighboring Doppler line for envelope alignment to obtain starting point value Min_track(j) and end point value Max_track(j) of line section of each type of the envelopes of the current Doppler line, wherein j is the serial number of the envelope, and j=0, 1, 2, . . . , N−1, and registering the starting point value Min_track(j) and the end point value Max_track (j) of the line section of each type of the envelopes of the current Doppler line in an internal register of the logic device.

In one embodiment, an envelope encoding and spectrum data combination module is provided for reading out the spectrum data of the current Doppler line as well as the starting point value Min_track(j) and the end point value Max_track(j) of the line section of each type of the envelopes of the current Doppler line from the embedded memory of the logic device; with respect to each of the spectrum data dots on the current Doppler line, within the transmission clock cycle corresponding to each of the spectrum data dots and dot by dot: (1) calculating the serial number Dot_NO=i+1 of a current spectrum data dot on the current Doppler line, wherein i=0, 1, 2, . . . , K−1, and K is the number of the spectrum data dots on the current Doppler line; (2) comparing the Dot_NO value corresponding to the current spectrum data dot on the current Doppler line with the starting point value Min_track(j) and the end point value Max_track(j) of the line section of each type of the envelopes of the current Doppler line; if the Dot_NO value corresponding to the current spectrum data dot on the current Doppler line is between the starting point value Min_track(j) and the end point value Max_track(j) of line section of a certain type of envelope of the current Doppler line, an envelope code Track_code[j] corresponding to that type of envelope is 1, otherwise the envelope code Track_code[j] corresponding to that type of envelope is 0; whereby a N-bit envelope code Track_code[N−1:0] is obtained; (3) combining the N-bit envelope code Track_code[N−1:0] with the spectrum data value corresponding to the current spectrum data dot on the current Doppler line to obtain combined Doppler data, and storing the combined Doppler data in a scan conversion memory, wherein the number N of the types of the envelopes is smaller than difference between bit width of the scan conversion memory and that of the spectrum data.

The apparatus may further include an envelope superposition module for reading out the combined Doppler data from the scan conversion memory; performing a logic operation on the N-bit envelope code Track_code[N−1:0] in the combined Doppler data and a N-bit selective value for envelope switching Track_switch[N−1:0] set by the system to obtain a N-bit envelope code selected by envelope switching Switch_out[N−1:0]; sending the N-bit envelope code selected by envelope switching Switch_out[N−1:0] to a N-bit priority encoder to obtain a L-bit priority-encoded envelope value Encode[L−1:0], wherein L=log 2N+1; sending the L-bit priority-encoded envelope value Encode[L−1:0] to a 1-of-N+1 selector to output the envelope value which is finally chosen to display among N types of the envelopes or the spectrum data value to a display module for displaying.

Advantageously, logic device and memories (SSRAM, SDRAM and DDR, etc.) are utilized to implement the Doppler scan conversion. The use of a memory out of the logic device with a large capacity instead of the restricted embedded memory resources does not significantly increase the overhead of the logic resources or decrease the efficiency of the system, even when the number of envelopes increases, and supports the real-time switching among multiple types of envelopes. Therefore, in comparison with conventional implementations of Doppler scan conversion, with the increase of the number of envelopes that can be displayed, the disclosed technique improves the switching of the envelopes and saves the restricted embedded memory resources, providing flexibility, high efficiency, and low cost.

Figure 4:
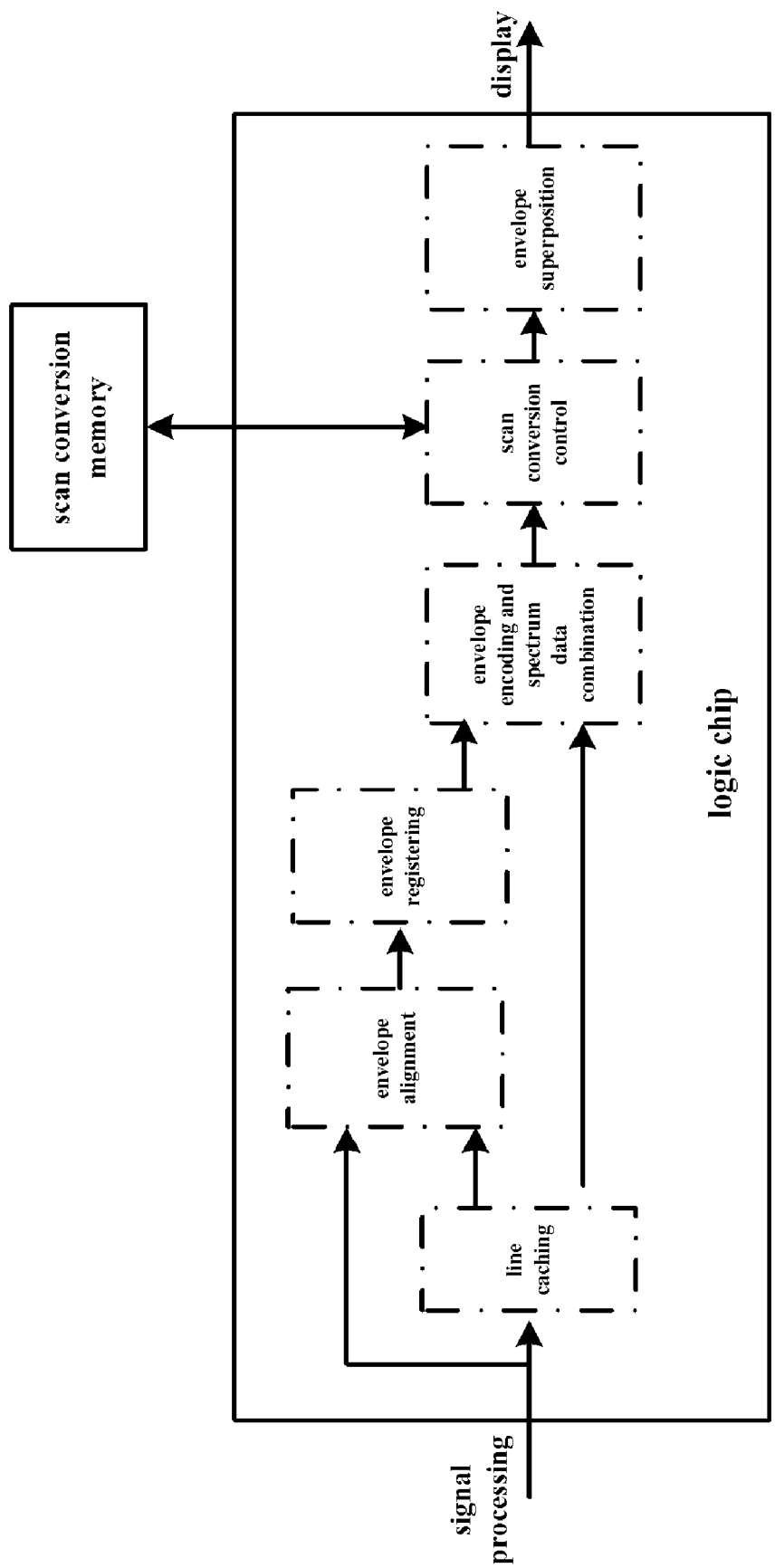
FIG. 4 is a block diagram of the implementation of Doppler scan conversion according to one embodiment of the present disclosure.

FIG. 4 illustrates a block diagram of an implementation of Doppler scan conversion according to one embodiment of the present disclosure. Since each type of envelope of each scanning line in a Doppler image is only one dot, the finally displayed envelopes may be discontinuous if only such dots are displayed. To make the envelopes continuous, the envelope dots of two adjacent scanning lines need to be aligned according to certain rules. The basic rule for envelope alignment is that the aligned envelope can enclose the spectrogram.

The implementation of envelope alignment is shown in FIGS. 5(a)-(b). As shown in FIG. 5(a), if the value of a certain type of envelope on the No. i Doppler line (corresponding to the location of that type of the envelope on the No. i Doppler line, as shown by the solid dot in FIG. 5(a)) is smaller than that of the same type of envelope on the No. i+1 Doppler line (as shown by the solid rectangle in FIG. 5(a)), that type of the envelope on the No. i Doppler line needs to be aligned through the supplement of dots on the No. i Doppler line (as shown by the hollow circles in FIG. 5(a)).

On the other hand, as shown in FIG. 5(b), if the value of a certain type of envelope on the No. i Doppler line (as shown by the solid dot in FIG. 5(b)) is greater than that of the same type of envelope on the No. i+1 Doppler line (as shown by the solid rectangle in FIG. 5(b)), the same type of envelope on the No. i+1 Doppler line needs to be aligned through the supplement of dots on the No. i+1 Doppler line (as shown by the hollow rectangles in FIG. 5(b)). After the envelope alignment, each type of envelope becomes a line section on each Doppler line, said line section being represented by a starting point Min_track(j) and an end point Max_track(j), wherein j=0, 1, 2, ..., N−1, j being the serial number of envelopes. According to present disclosure, since the encoded envelope values together with the spectrum data of the scanning line where the envelopes lie are written in the scan conversion memory, the image data of the current Doppler line, including the envelopes and the spectrum data, need to be cached during the envelope alignment.

After the envelope alignment, the starting point Min_track(j) and the end point Max_track(j) of the line section of each type of the envelopes are registered for the subsequent envelope encoding and spectrum data combination.

FIG. 6 is a block diagram of an implementation of envelope encoding and spectrum data combination according to one embodiment of the present disclosure. The envelope encoding and spectrum data combination is performed once in a clock cycle corresponding to each of the spectrum data dots according to the time sequence shown in FIG. 3. In FIG. 6, Dot_NO is the count value of the spectrum data dots on the current Doppler line. Each time a new Doppler line arrives, the counter is cleared to zero and subsequently, when every Doppler spectrum data dot on the current Doppler line is received, the value of the counter is incremented, whereby the count value represents the serial number of the current Doppler spectrum data dot on the current Doppler line.

The value Dot_NO corresponding to each of the Doppler spectrum data dots is the vertical coordinate of the spectrum data dot on the display screen. The value Dot_NO corresponding to the current Doppler spectrum data dot is compared with the range (i.e. Min_track(j) and Max_track(j), wherein j=0, 1, 2, ..., N−1, corresponding to N types of the envelopes) of line section of each type of the envelopes on the current Doppler line obtained in the envelope alignment. If the value Dot_NO corresponding to the current Doppler spectrum data dot is within the range of a line section of a certain type of envelope on the current Doppler line, i.e., Max_track(j)≧the value Dot_NO corresponding to the current Doppler spectrum data dot≧Min_track(j), the envelope code Track_code[j] corresponding to that type of envelope is 1, showing that that type of envelope will replace the spectrum data dot and is thus displayed at the location on the screen where the spectrum data dot lies.

If the value Dot_NO corresponding to the current Doppler spectrum data dot is not within the range of line section of a certain type of envelope on the current Doppler line, the envelope code Track_code[j] corresponding to that type of envelope is 0, showing that that type of envelope will not be displayed at the location on the screen where the spectrum data dot lies. As there are multiple envelopes on each of the Doppler lines, various envelopes need to be displayed at a certain dot. However, since only the grey level corresponding to one type of envelope can be finally displayed on each dot, which type of the envelope will be displayed on that dot depends on the priority level for the grey level and the envelope switch (i.e. whether the envelope is to be displayed) set by the system. To be specific, when multiple envelopes are superposed and all of the envelope switches are on, the envelope with the highest priority level for the grey level will be displayed, which is embodied in the envelope superposition. After the value Dot_NO corresponding to the current Doppler spectrum data dot is compared with the range of line section of each of N types of envelopes on the current Doppler line, a N-bit envelope code Track_code[N−1:0] is obtained. The N-bit envelope code is combined with the spectrum data value of the current Doppler spectrum data dot according to the data format as shown in FIG. 7 to obtain a combined Doppler data.

Figure 7:
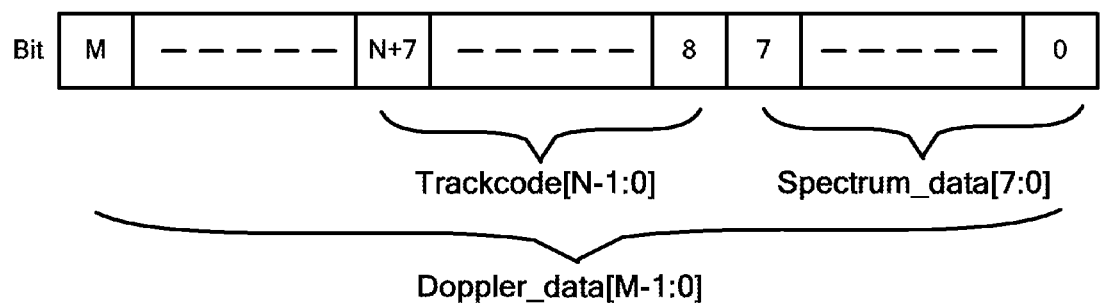
FIG. 7 is a data structure after the envelope encoding and spectrum data combination according to one embodiment of the present disclosure.

The composition of the combined Doppler data is shown in FIG. 7, wherein M is the bit width of the scan conversion memory. To ensure that no extra read-write of the scan conversion memory is generated due to the presence of the envelope code, the number N of the types of the envelopes should be smaller than the difference between the bit width M of the scan conversion memory and that of the spectrum data. Since the Doppler spectrogram is displayed generally in 256 grey levels, i.e., the bit width of the spectrum data is 8 bits, the number N of the types of the envelopes should be smaller than the bit width M of the scan conversion memory minus eight. The combined Doppler data obtained by the envelope encoding and spectrum data combination is written into the scan conversion memory through a scan conversion control module. The combined Doppler data stored in the scan conversion memory are read out in rows in a horizontally scanned VGA time sequence under the control of the scan conversion control module and sent to an envelope superposition module.

Figure 8:
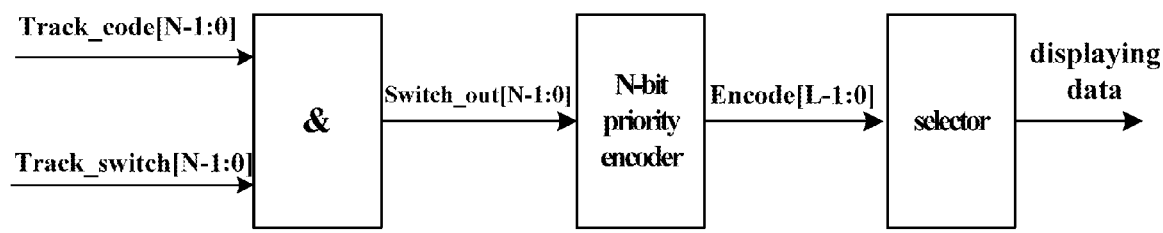
FIG. 8 is a block diagram of an implementation of envelope superposition according to one embodiment of the present disclosure.

The implementation of the envelope superposition module is shown in FIG. 8. In FIG. 8, Track_code is the envelope code bit of each of the spectrum data dot read out from the scan conversion memory, and Track_switch is the selective bit for the envelope switch set by the system software according to the envelope selected by the user, with each bit corresponding to each of the types of the envelopes. When a certain bit is 1, the envelope switch corresponding to that bit is on and the corresponding envelope is to be displayed; otherwise, the envelope switch is off and the corresponding envelope is not displayed.

As shown in FIG. 8, a "bit and &" logic operation may be performed on the N-bit envelope code (Track_code) in the combined Doppler data read out by the scan conversion control module and a N-bit selective value for the envelope switch set by the system software to obtain a N-bit envelope code for envelope switching selection (Switch_out). In addition, the N-bit envelope code for envelope switching selection (Switch_out) is sent to an N-bit priority encoder to obtain an L-bit priority-encoded envelope value (Encode), wherein L=log 2N+1. The reason for using the priority encoding is that when multiple envelopes are superposed at the same point, only the envelope with the highest priority level can be displayed. Finally, the priority-encoded envelope value is sent to a 1-of-N+1 (N is the number of the types of the envelopes) selector, the N+1 possible inputs of the selector corresponding to N types of envelopes or spectrum data that may be finally displayed, the output of the selector being the grey level of relevant envelope corresponding to N types of envelopes or spectrum data (if there is no envelope to be displayed at that dot, the spectrum data will be displayed), and the output being sent to a display module for display.

The relationship between the input/output of the priority encoder and input/output of the selector is shown in Table 1, with the grey level of each type of the envelopes being set by the system. As only the envelope with the highest priority level can be displayed when multiple envelopes are superposed at the same point, it should be ensured that the envelope data is transmitted in the order of the priority from low to high in the data transmission format as shown in FIG. 3, in the implementation of envelope superposition according to the method of the present disclosure.

TABLE 1

Input/output of the priority encoder and the input/output of the selector

| Priority encoder input | Priority encoder output/Selector input | Selector output |
|---|---|---|
| 1X . . . XX | 0 | Grey level of Envelope 1 |
| 01 . . . XX | 1 | Grey level of Envelope 2 |
| . . . | . . . | . . . |
| 000 . . . 1X | N − 2 | Grey level of Envelope N − 1 |
| 000 . . . 01 | N − 1 | Grey level of Envelope N |
| 000 . . . 00 | N | Value of spectrum data |

Detailed descriptions of several example embodiments are provided above. However, the invention is not restricted to these example embodiments. Without departing from the scope of the invention, those skilled in this art may make changes and modifications, which will all fall into the claims of the invention.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

As used herein, a software module or component may include any type of computer instruction or computer executable code located within a memory device and/or transmitted as electronic signals over a system bus or wired or wireless network. A software module may comprise, for instance, one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

The invention claimed is:

1. A method for Doppler scan conversion, comprising:

caching image data of a current Doppler line, which includes spectrum data and values of N types of envelopes, in an embedded memory of a logic device;

comparing the value of each type of the envelopes of the current Doppler line with that of the same type of envelope of a neighboring Doppler line for envelope alignment to obtain a starting point value Min_track(j) and an end point value Max_track(j) of line section of each type of the envelopes of the current Doppler line, wherein j is the serial number of the envelope, and j=0, 1, 2, ..., N−1, and registering the starting point value Min_track(j) and the end point value Max_track(j) of the line section of each type of the envelopes of the current Doppler line in an internal register of the logic device;

reading out the spectrum data of the current Doppler line as well as the starting point value Min_track(j) and the end point value Max_track(j) of the line section of each type of the envelopes of the current Doppler line from the embedded memory of the logic device;

with respect to each dot of the spectrum data on the current Doppler line, within the transmission clock cycle corresponding to each of the spectrum data dots and dot by dot:

(1) calculating the serial number Dot_NO=i+1 of a current spectrum data dot on the current Doppler line, wherein i=0, 1, 2, ..., K−1, and K is the number of the spectrum data dots on the current Doppler line;

(2) comparing the Dot_NO value corresponding to the current spectrum data dot on the current Doppler line with the starting point value Min_track(j) and the end point value Max_track(j) of the line section of each type of the envelopes of the current Doppler line; if the Dot_NO value corresponding to the current spectrum data dot on the current Doppler line is between the starting point value Min_track(j) and the end point value Max_track(j) of line section of a certain type of envelope of the current Doppler line, an envelope code Track_code[j] corresponding to that type of envelope is 1; otherwise the envelope code Track_code[j] corresponding to that type of envelope is 0; whereby a N-bit envelope code Track_code[N−1:0] is obtained;

(3) combining the N-bit envelope code Track_code[N−1:0] with the spectrum data value corresponding to the current spectrum data dot on the current Doppler line to obtain combined Doppler data, and storing the combined Doppler data in a scan conversion memory, wherein the number N of the types of the envelopes is smaller than difference between bit width of the scan conversion memory and that of the spectrum data.

2. The method according to claim 1, further comprising:

reading out the combined Doppler data from the scan conversion memory;

performing a logic operation on the N-bit envelope code Track_code[N−1:0] in the combined Doppler data and a N-bit selective value for envelope switching Track_switch[N−1:0] set by the system to obtain a N-bit envelope code selected by envelope switching Switch_out[N−1:0];

sending the N-bit envelope code selected by envelope switching Switch_out[N−1:0] to a N-bit priority encoder to obtain a L-bit priority-encoded envelope value Encode[L−1:0] wherein L=$\log_2 N$+1;

sending the L-bit priority-encoded envelope value Encode[L−1:0] to a 1-of-N+1 selector to output the envelope value which is finally chosen to display among N types of the envelopes or the spectrum data value to a display module for displaying.

3. The method according to claim 2, wherein a relationship between input/output of the priority encoder and that of the selector is defined as in the table below:

| Priority encoder input | Priority encoder output/Selector input | Selector output |
| --- | --- | --- |
| 1X ... XX | 0 | Grey level of Envelope 1 |
| 01 ... XX | 1 | Grey level of Envelope 2 |
| ... | ... | ... |
| 000 ... 1X | N − 2 | Grey level of Envelope N − 1 |
| 000 ... 01 | N − 1 | Grey level of Envelope N |
| 000 ... 00 | N | Value of spectrum data. |

4. The method according to claim 2, wherein the logic operation is a "bit and &" operation.

5. The method according to claim 1, wherein the embedded memory is an FGPA embedded memory.

6. The method according to claim 1, wherein the embedded memory is selected from the group consisting of a CPLD embedded memory and an ASIC embedded memory.

7. The method according to claim 1, further comprising:

if the value of a certain type of envelope of the current Doppler line is smaller than that of the same type of envelope of the neighboring Doppler line, aligning that type of the envelope of the current Doppler line through the supplement of dots on the current Doppler line;

if the value of a certain type of envelope of the current Doppler line is greater than that of the same type of envelope of the neighboring Doppler line, aligning that type of the envelope of the neighboring Doppler line through the supplement of dots on the neighboring Doppler line.

8. The method according to claim 1, wherein the number N of the types of the envelopes is smaller than the bit width of the scan conversion memory minus eight.

9. An apparatus for Doppler scan conversion, comprising:

a line caching module for caching image data of a current Doppler line in an embedded memory of a logic device, said image data including spectrum data and values of N types of envelopes;

an envelope alignment module for comparing a value of each type of the envelopes of the current Doppler line with that of the same type of envelope of a neighboring Doppler line for envelope alignment to obtain a starting point value Min_track(j) and an end point value Max_track(j) of a line section of each type of the envelopes of the current Doppler line, wherein j is the serial number of the envelope, and j=0, 1, 2, ..., N−1, and registering the starting point value Min_track(j) and the end point value Max_track(j) of the line section of each type of the envelopes of the current Doppler line in an internal register of the logic device;

an envelope encoding and spectrum data combination module for reading out the spectrum data of the current Doppler line as well as the starting point value Min_track(j) and the end point value Max_track(j) of the line section of each type of the envelopes of the current Doppler line from the embedded memory of the logic device; with respect to each of the spectrum data dots on the current Doppler line, within the transmission clock cycle corresponding to each of the spectrum data dots and dot by dot: (1) calculating the serial number Dot_NO=i+1 of a current spectrum data dot on the current Doppler line, wherein i=0, 1, 2, ..., K−1, and K is the number of the spectrum data dots on the current Doppler line; (2) comparing the Dot_NO value corresponding to the current spectrum data dot on the current Doppler line with the starting point value Min_track(j) and the end point value Max_track(j) of the line section of each type of the envelopes of the current Doppler line; if the Dot_NO value corresponding to the current spectrum data dot on the current Doppler line is between the starting point value Min_track(j) and the end point value Max_track(j) of the line section of a certain type of envelope of the current Doppler line, an envelope code Track_code[j] corresponding to that type of envelope is 1; otherwise the envelope code Track_code[j] corresponding to that type of envelope is 0; whereby a N-bit envelope code Track_code [N−1:0] is obtained; (3) combining the N-bit envelope code Track_code[N−1:0] with the spectrum data value corresponding to the current spectrum data dot on the current Doppler line to obtain the combined Doppler data, and storing the combined Doppler data in a scan conversion memory, wherein the number N of the types of the envelopes is smaller than a difference between the bit width of the scan conversion memory and that of the spectrum data.

10. The apparatus according to claim 9, further comprising:
an envelope superposition module for reading out the combined Doppler data from the scan conversion memory; performing a logic operation on the N-bit envelope code Track_code[N−1:0] in the combined Doppler data and a N-bit selective value for envelope switching Track_switch[N−1:0] set by the system to obtain a N-bit envelope code selected by envelope switching Switch_out[N−1:0]; sending the N-bit envelope code selected by envelope switching Switch_out[N−1:0] to a N-bit priority encoder to obtain a L-bit priority-encoded envelope value Encode[L−1:0], wherein L=$\log_2^N$+1; sending the L-bit priority-encoded envelope value Encode[L−1:0] to a 1-of-N+1 selector to output the envelope value which is finally chosen to display among N types of the envelopes or the spectrum data value to a display module for displaying.

11. The apparatus according to claim 10, wherein a relationship between input/output of the priority encoder and that of the selector is defined as in the table below:

| Priority encoder input | Priority encoder output/ Selector input | Selector output |
| --- | --- | --- |
| 1X ... XX | 0 | Grey level of Envelope 1 |
| 01 ... XX | 1 | Grey level of Envelope 2 |
| ... | ... | ... |
| 000 ... 1X | N − 2 | Grey level of Envelope N − 1 |
| 000 ... 01 | N − 1 | Grey level of Envelope N |
| 000 ... 00 | N | Value of spectrum data. |

12. The apparatus according to claim 10, wherein the logic operation is a "bit and &" operation.

13. The apparatus according to claim 9, wherein the embedded memory is an FGPA embedded memory.

14. The apparatus according to claim 9, wherein the embedded memory is selected from the group consisting of a CPLD embedded memory and an ASIC embedded memory.

15. The apparatus according to claim 9, wherein:
if the value of a certain type of envelope of the current Doppler line is smaller than that of the same type of envelope of the neighboring Doppler line, that type of the envelope of the current Doppler line is aligned through the supplement of dots on the current Doppler line;
if the value of a certain type of envelope of the current Doppler line is greater than that of the same type of envelope of the neighboring Doppler line, that type of the envelope of the neighboring Doppler line is aligned through the supplement of dots on the neighboring Doppler line.

16. The apparatus according to claim 9, wherein the number N of the types of the envelopes is smaller than the bit width of the scan conversion memory minus eight.

* * * * *